US00PP33645P2

(12) United States Plant Patent
Kirwan

(10) Patent No.: US PP33,645 P2
(45) Date of Patent: Nov. 16, 2021

(54) ***AGLAONEMA* PLANT NAMED 'OSVAG2'**

(50) Latin Name: ***Aglaonema* hybrid**
Varietal Denomination: OSVAG2

(71) Applicant: ForemostCo., Inc., Miami, FL (US)

(72) Inventor: David Kirwan, Winter Garden, FL (US)

(73) Assignee: ForemostCo., Inc., Miami, FL (US)

( * ) Notice: Subject to any disclaimer, the term of this patent is extended or adjusted under 35 U.S.C. 154(b) by 0 days.

(21) Appl. No.: 16/924,393

(22) Filed: Jul. 9, 2020

(51) Int. Cl.
*A01H 5/12* (2018.01)
*A01H 6/10* (2018.01)
*A01H 5/02* (2018.01)
*A01H 6/00* (2018.01)

(52) U.S. Cl.
USPC ..... Plt./376
CPC ..... *A01H 5/02* (2013.01); *A01H 6/00* (2018.05)

(58) Field of Classification Search
USPC ..... Plt./376
See application file for complete search history.

*Primary Examiner* — Susan McCormick Ewoldt
(74) *Attorney, Agent, or Firm* — The Webb Law Firm

(57) ABSTRACT

A new and distinct *Aglaonema* plant having pink and green colored leaves and pink colored stems.

3 Drawing Sheets

Botanical classification: Interspecific *Aglaonema* hybrid.
Varietal denomination: 'OSVAG2'.

BACKGROUND OF THE INVENTION

The present invention comprises a new and distinct variety of *Aglaonema* plant having the varietal name of 'OSVAG2'. 'OSVAG2' is the result of a cross conducted in Costa Rica between *Aglaonema* hybrid variety known as "Diamond Duke" (female parent, unpatented) and *Aglaonema* hybrid variety known as "Starlite Simone" (male parent, unpatented). The new variety was selected in August of 2018 in Costa Rica. Asexual reproductions of the new variety by cuttings first occurred in April of 2019. The new variety is similar to its female and male parents in leaf midrib, stem, and petiole colors. However, "Diamond Duke" exhibits less leaf variegation and coloration spreading from the midrib than 'OSVAG2'. Further, the leaf venation of "Starlite Simone" is more pronounced than that of 'OSVAG2'. 'OSVAG2' has been trial and field tested and has been found to retain its distinctive characteristics and remain true to type through successive propagations. The present invention has not been evaluated under all possible environmental conditions. The phenotype may vary with variations in environment without a change in the genotype of the plant.

Similar to an unnamed and unpatented *Aglaonema* variety known to the breeder, 'OSVAG2' exhibits pink and green colored leaves, pink colored midribs and stems, and green colored leaf margins. However, the varieties differ in that the leaves of the comparison variety are narrower, have more pink coloration spreading from their midribs, and have more outlined venation. When compared to *Aglaonema* variety named 'OSVAG1' (U.S. Plant patent application Ser. No. 16/924,357), the new variety is similar in leaf size and shape. However, 'OSVAG1' exhibits red and green colored leaves. Further, the following characteristics distinguish 'OSVAG2' from other *Aglaonema* varieties known to the breeder:

Pink colored stems and petioles;
Green colored leaf margins;
Leaf midribs that transition from dark pink to green coloration; and
Venation that differs from pink to green in color.

DESCRIPTION OF THE DRAWINGS

The accompanying photographic drawings taken at approximately 18 months of age illustrate the new variety, with the colors being as nearly true as is possible with color illustrations of this type.

DESCRIPTION OF THE PLANT

Figure 1:
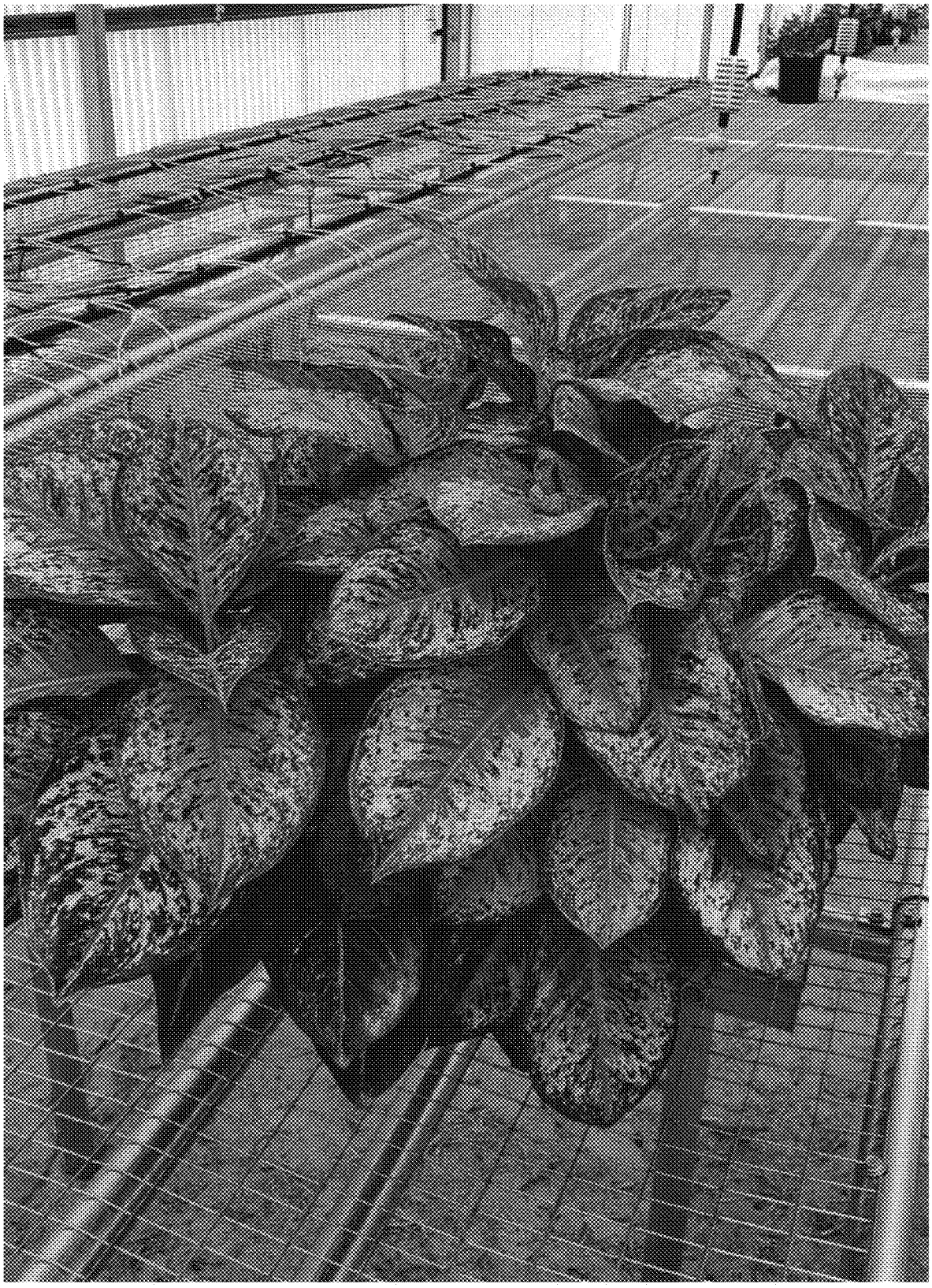
FIG. 1 shows a plant of the new variety.
Figure 2:
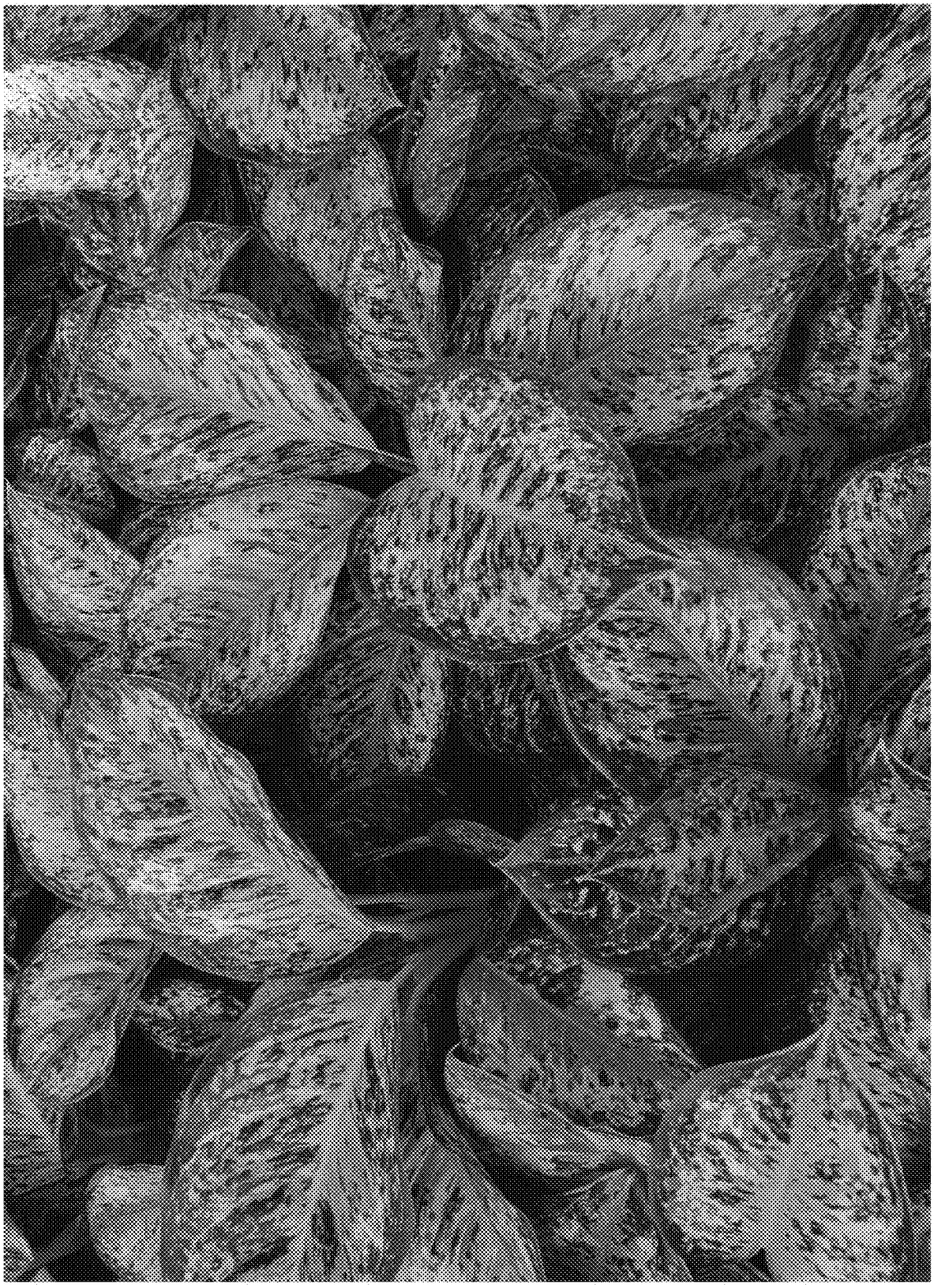
FIG. 2 shows a close-up view of the foliage of multiple plants of the new variety.
Figure 3:
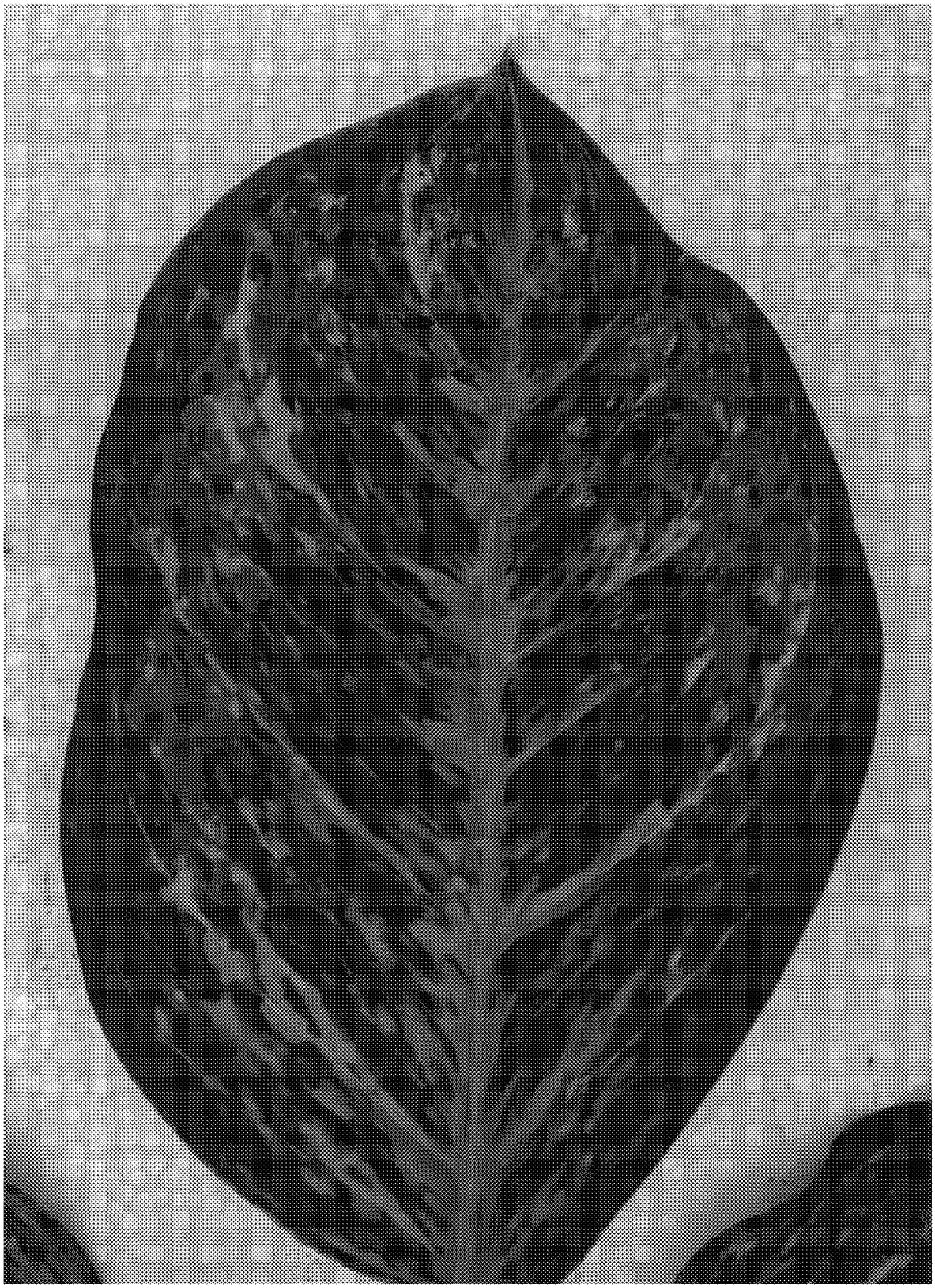
FIG. 3 shows a close-up view of the upper leaf surface of the new variety.

The following detailed description sets forth the characteristics of the new variety at approximately 18 months of age. The data which defines these characteristics was collected in a greenhouse in June of 2020 in Miami, Fla. Plants of the new variety were grown under 2,500 foot candles of artificial light in 2 gallon pots in a greenhouse in Miami, Fla. having 70% relative humidity and average temperatures from 18-29° C. Color references are primarily to the Munsell Plant Tissue Color Book, 2019 publication, except where general color terms are used.

PLANT

Time to initiate roots: About 25 days at about 26° C.
Time to develop roots: About 25 days at about 26° C.
Time to produce a finished plant from a rooted cutting: About 8 weeks in a 15 cm container.
Rooting habit and description: Roots spread out from the side and are 2.5Y 8/4, 7.5R 5/8 and 2.5GY 6/6 in color.

Form: Spreading.
Height from media surface to top of foliage: 24.8 cm.
Height from media surface to top of inflorescence: 17.8 cm.
Plant diameter: 45.7 cm.
Plant shape: Clumping, with upright and outwardly turned leaves.
Vigor: Strong.
Strength: Pliable, with no need for artificial support.
Disease resistance/susceptibility: Susceptible to *Erwinia*.
Pest resistance/susceptibility: Susceptible to mealybugs.
Temperature tolerance: Sensitive to temperatures below 13° C. or above 29° C.
Drought tolerance: None.
Seeds/fruit: None present.
Stem:
*Average number/clumps of leaves per plant.*—7.
*Aspect.*—Vertical and upright and turned outward about 40°.
*Length.*—14.6 cm.
*Diameter.*—1.3 cm.
*Shape.*—Vertical column.
*Color.*—Green and pink (10R 7/4 and 2.5GY 6/8).
*Texture.*—Smooth and leathery.
*Strength.*—Sturdy, but pliable.
*Internode length.*—3.0 cm.
Leaves:
*Arrangement.*—Opposite.
*Average number per plant.*—7.
*Length.*—18.4 cm.
*Width.*—10.2 cm.
*Shape of leaf (generally).*—Ovate.
*Shape of apex.*—Acute.
*Shape of base.*—Acute.
*Margin description.*—Entire.
*Aspect.*—Symmetric.
*Texture and luster.*—Upper surface: Smooth and leathery with creases along the veins and a silky luster. Lower surface: Smooth and leathery with creases along the veins and a silky luster.
*Pubescence.*—Upper surface: None present. Lower surface: None present.
*Fragrance.*—None present.
*Color.*—Young leaves: Upper surface: Green and pink (2.5R 5/10 — along the midrib going out towards the veins; 2.5R 5/8 — spotting along the veins; 5GY 5/4 — surrounding spotting; 2.5 GY 7/4 — surrounding the veins and spotting; and 7.5GY 3/2 — along the margin and in between the veins). Lower surface: Green and pink (5GY 4/6 — along the margins and in between the veins; 2.5R 5/10 — in between the veins; and 2.5R 7/6 — along the midrib). Mature leaves: Upper surface: Green and pink (2.5R 5/10 — along the midrib going into the veins; 7.5GY 3/2 — along the margin and in between the veins; 2.5GY 6/6 — spotting in between the veins; 2.5GY 7/4 — surrounding spotting; and 2.5GY 8/6 — in between the veins, closer to the margin). Lower surface: Mostly green with some pink color present (2.5R 5/10 — along the veins; 2.5R 7/6 — in between the veins and along the midrib; and 5GY 4/6 — along the margin and in between the veins).
*Veins.*—Venation pattern: Pinnate. Color: Upper surface: Light pink, pink, magenta, light green, and green (2.5R 5/10, 2.5R 5/8, 7.5GY 4/6 and 2.5GY 5/6). Lower surface: Light pink and light green (2.5R 5/10, 2.5R 7/6 and 5GY 4/6).
Petioles:
*Aspect.*—Upright, with a 40-45° upward turn.
*Length.*—10.7 cm.
*Diameter.*—0.6 cm.
*Color.*—Pink (2.5R 6/6).
*Strength.*—Strong and lightly flexible.
*Wing.*—Not present.

INFLORESCENCE DESCRIPTION

Buds:
*Shape.*—Oval; egg-shaped.
*Length of an individual bud.*—3.8 cm.
*Diameter of an individual bud.*—1.3 cm.
*Color.*—Green (5GY 5/8).
*Texture.*—Smooth and leathery.
Inflorescences:
Natural flowering season: Year-round in Miami, Fla.
Blooming habit: Continuous.
Inflorescence arrangement: Spadix in spathe.
Orientation at opening: Circular opening from the side.
Inflorescence position: Tends to form below the foliage, but sometimes above.
Number of inflorescences per plant: 2-3.
Lastingness of an individual flower: 5 weeks or more.
Inflorescence length: 3.8 cm.
Inflorescence diameter: 1.3 cm.
Flowers:
*Type.*—Simple.
*Length.*—3.8 cm.
*Diameter.*—2.0 cm.
*Depth.*—1.7 cm.
Spathe:
*Length.*—3.6 cm.
*Width.*—5.1 cm.
*Color.*—5GY 5/6 (inner and outer surfaces).
Spadix:
*Length.*—3.3 cm.
*Diameter.*—1.3 cm.
*Color.*—5Y 8/12.
Peduncle:
*Length.*—3.8 cm.
*Diameter.*—1.3 cm.
*Color.*—5GY 5/8.
Petals: Not applicable.
Fragrance: None present.

REPRODUCTIVE ORGANS

Stamens:
*Number.*—About 13.
*Filament.*—Length: 0.5 cm. Color: 5Y 8/12.
*Anthers.*—Shape: Circular. Length: 0.1 cm. Color: 5Y 8/12.
*Pollen.*—Color: 5Y 8/12. Amount: Not visible to the naked eye.

Pistils:

*Number*.—More than 250.

*Length*.—0.6 cm.

*Style*.—Length: 0.6 cm. Color: 2.5Y 8/4.

*Stigma*.—Shape: Capitate. Color: 2.5Y 8/4. Size: Small.

*Ovaries*.—Position: Inferior — attached beneath flowers. Length: Under 0.01 cm. Width: Under 0.01 cm. Color: 2.5Y 8/4.

I claim:

1. A new and distinct variety of *Aglaonema* plant, as is herein illustrated and described.

* * * * *